(12) United States Patent
Morel (10) Patent No.: US 11,583,585 B2
(45) Date of Patent: Feb. 21, 2023

(54) GOLD NANOPARTICLES AND ECOLOGICAL METHOD OF PRODUCTION

(71) Applicant: TORSKAL, Sainte-Clotilde (FR)

(72) Inventor: Anne-Laure Morel, Sainte-Marie (FR)

(73) Assignee: Torskal, Sainte-Clotilde (FR)

( * ) Notice: Subject to any disclaimer, the term of this patent is extended or adjusted under 35 U.S.C. 154(b) by 566 days.

(21) Appl. No.: 16/069,479

(22) PCT Filed: Jan. 23, 2017

(86) PCT No.: PCT/FR2017/050131
§ 371 (c)(1),
(2) Date: Jul. 11, 2018

(87) PCT Pub. No.: WO2017/125695
PCT Pub. Date: Jul. 27, 2017

(65) Prior Publication Data
US 2019/0022234 A1 Jan. 24, 2019

(30) Foreign Application Priority Data
Jan. 22, 2016 (FR) ...................................... 1650520

(51) Int. Cl.
*A61K 47/46* (2006.01)
*B22F 9/24* (2006.01)
(Continued)

(52) U.S. Cl.
CPC ............ *A61K 47/46* (2013.01); *A61K 8/0245* (2013.01); *A61K 8/19* (2013.01); *A61K 8/498* (2013.01); *A61K 8/602* (2013.01); *A61K 8/9789* (2017.08); *A61K 9/51* (2013.01); *A61K 9/5115* (2013.01); *A61K 33/242* (2019.01); *A61K 47/22* (2013.01); *A61K 47/26* (2013.01); *A61K 49/04* (2013.01);
(Continued)

(58) Field of Classification Search
CPC .......... A61K 2800/10; A61K 2800/413; A61K 33/24; A61K 47/46; A61K 8/0245; A61K 8/19; A61K 8/602; A61K 8/9789; A61K 9/51; A61K 9/5115; A61P 35/00; A61Q 19/00; B22F 1/0018; B22F 1/0044; B22F 2001/0037; B22F 2301/255; B22F 2304/054; B22F 9/24
See application file for complete search history.

(56) References Cited

U.S. PATENT DOCUMENTS 8,333,994 B2 12/2012 Katti et al.

FOREIGN PATENT DOCUMENTS

WO 2005095031 10/2005

OTHER PUBLICATIONS

Levchenko et al., Synthesis and study of gold nanoparticles stabilized by bioflavonoids, Seriya Khimicheskaya, No. 3, pp. 417-424, Mar. 2011. (Year: 2011).*

(Continued)

*Primary Examiner* — Melissa S Mercier
(74) *Attorney, Agent, or Firm* — TraskBritt (57) ABSTRACT

A method of preparing biocompatible and stable gold nanoparticles comprises preparing at least one flavonoid-rich plant extract, and mixing at least one of the plant extracts with an aqueous solution of at least one gold salt. The flavonoid-rich plant extract is an extract of *Hubertia ambavilla* or *Hypericum lanceolatum*. The gold nanoparticles may be used for medical and/or cosmetic purposes.

5 Claims, 10 Drawing Sheets

(51) Int. Cl.
- A61K 9/51 (2006.01)
- A61K 33/242 (2019.01)
- B22F 1/07 (2022.01)
- B22F 1/054 (2022.01)
- A61K 8/02 (2006.01)
- A61K 8/19 (2006.01)
- A61K 8/60 (2006.01)
- A61K 49/04 (2006.01)
- A61K 49/22 (2006.01)
- A61K 8/9789 (2017.01)
- A61K 8/49 (2006.01)
- A61K 47/22 (2006.01)
- A61K 47/26 (2006.01)
- A61Q 19/00 (2006.01)

(52) U.S. Cl.
CPC ............ *A61K 49/222* (2013.01); *A61Q 19/00* (2013.01); *B22F 1/054* (2022.01); *B22F 1/07* (2022.01); *B22F 9/24* (2013.01); *A61K 2800/10* (2013.01); *A61K 2800/413* (2013.01); *B22F 1/0553* (2022.01); *B22F 2301/255* (2013.01); *B22F 2304/054* (2013.01)

(56) References Cited

OTHER PUBLICATIONS

Chaudhuri et al., Gold-Based Core/Shell and Hollow Nanoparticles, First published: Jul. 19, 2013, downloaded at <https://doi.org/10.1002/0471238961.goldpari.a01> (Year: 2013).*

Levchenko (Synthesis and study of gold nanoparticles stabilized by bioflavonoids, Russian Chemical Bulletin, International Edition, vol. 60, No. 3, pp. 426-433, Mar. 2011 (Year: 2011).*

Wabo et al. ("Phenolic Compounds and Terpenoids from Hypericum lanceolatum" Rec. Nat. Prod. 6:2 (2012) 94-100) (Year: 2012).*

Chaudhuri et al. (Gold-Based Core/Shell and hollow Nanoparticles, First published: Jul. 19, 2013). (Year: 2013).*

Paz et al. (Green synthesis of gold nanoparticles using plant extracts as reducing agents, Int J Nanomedicine, 2014; 9:4007-4021). (Year: 2014).*

Arifin et al., Trimodal Gadolinium-Gold Microcapsules Containing Pancreatic Islet Cells Restore Normoglycemia in Ciabetic Mice and can be Tracked by Using US CT, and Positive-Contrast MR Imaging, Radiology, vol. 260, No. 3, (Sep. 2011), pp. 790-798.

Boote et al., Gold Nanoparticle Contrast in a Phantom and Juvenile Swine: Models for Molecular Imaging of Human Organs Using X-Ray Computed Tomography, Acad Radiol., vol. 17, No. 4, (Apr. 2010), pp. 410-417.

Clark, III et al., Mathematical Model that Describes the Transition from Thermal to Photochemical Damage in Retinal Pigment Epithelial Cell Culture, Journal of Biomedical Optics, vol. 16, No. 2, (Feb. 2011), pp. 020504-1-020504-3.

Cujic et al., Optimization of Polyphenols Extraction from Dried Chokeberry Using Maceration as Traditional Technique, Food Chemistry, vol. 194, (2016), pp. 135-142.

Das et al., Biosynthesis of Stabilized Gold Nanoparticle Using an Aglycone Flavonoid, Quercetin, journal of Experimental Nanoscience, vol. 8, Issue 4, (2013), pp. 649-655 (abstract only).

Elia et al., Green Synthesis of Gold Nanoparticles Using Plant Extracts as Reducing Agents, International Journal ol Nanomedicine, vol. 9, (2014), pp. 4007-4021.

Frens et al., Controlled Nucleation for the Regulation of the Particle Size in Monodisperse Gold Suspensions, Nature Physical Science, vol. 241, (Nov. 6, 1072), pp. 20-22.

Huang et al., Plasmonic Photo-Thermal Therapy (PPTT), Alexandria Journal of Medicine, vol. 47, (2011), pp. 1-9.

International Search Report for International Application No. PCT/FR2017/050131 dated Apr. 18, 2017, 2 pages.

International Written Opinion for International Application No. PCT/FR2017/050131 dated Apr. 18, 2017, 5 pages.

Jabeen et al., Au-Nanomaterials as a Superior Choice for Near-Infrared Photothermal Therapy, Molecules, vol. 19, (2014), pp. 20580-20593.

Jiang et al., Near-Infrared Light Activatable Multimodal Gold Nanostructures Platform: An Emerging Pardigm for Cancer Therapy, CUrr Cancer Drug Targets, vol. 15, No. 5, pp. 406-422.

Ke et aL., Gold Nanoshelled Liquid Perfluorocarbon Nanocapsules for Combined Dual Modal Ultrasound/CT Imaging and Photothermal Therapy of Cancer, Nano Micro Small, vol. 10, No. 6, (2014), pp. 1220-1227.

Krishnaswamy et al., Value-Adding to Grape Waste: Green Synthesis of Gold Nanoparticles, Journal of Food Engineering, vol. 142, (2014), pp. 210-220.

Kumar et al., Plant-Mediated Synthesis of Silver and Gold Nanoparticles and their Applications, Journal of Chemical Technology and Biotechnology, vol. 84, Issue 2, (Feb. 2009), pp. 151-157 (abstract only).

Li et al., A Three-Temperature Model of Selective Photothermolysis for Laser Treatment of Port Wine Stain Containing Large Malformed Blood Vessels, Applied Thermal Engineering, vol. 65, (2014), pp. 308-321.

Mackey et al., The Most Effective Gold Nanorod Size for Plasmonic Photothermal Therapy: Theory and In Vitro Experiments, The Journal of Physical Chemistry B, vol. 118, (2014), pp. 1319-1326.

Nabil et al., Modelling Mass and Heat Transfer in Nano-Based Cancer Hyperthermia, Royal Society Open Science, vol. 2, 150447, http//dx.doi.org/10.1098/rsos. 150447, 17 pages.

Peeters et al., Mechanisms of Nanoparticle-Mediated Photomechanical Cell Damage, Biomedical Optics Express, vol. 3, No. 3, (Mar. 1, 2012), pp. 435-446.

Shibu et al., Nanomaterials Formations for Photothermal and Photodynamic Therapy of Cancer, Journal of Photochemistry and Photobiology C: Photochemistry Reviews, vol. 15, (2013), pp. 53-72.

Song et al., Near-IR Responsive Nanostructures for Nanobiophotonics: Emerging Impacts on Manomedicine, Basic Science, Nanomedicine: Nanotechnology, Biology, and Medicin, vol. 12, (2016), pp. 771-788.

Stylianopoulos et al., Design Considerations for Nanotherapeutics in Oncology, Nanomedicine: Nanotechnology, Biology, and Medicine vol. 11, (2015), pp. 1893-1907.

Furkevich et al., A Study of the Nucleation and Growth Processes in the Synthesis of Colloidal Gold, Discussions of the Faraday Society, vol. 11, (1951), 55-75.

Upendran et al., Gold Nanoparticle Based X-Ray Contrast Agent for Tumor Imaging in Mice and Dog: A Potential Nano-Platform for Computer Tomography Theranostics, J. Biomed Nanotechnol. voll. 10, No. 3, (Mar. 2014), pp. 383-392.

Xu et al., Synthesis, Characterization, and In Vitro Evaluation of Targeted Gold Nanoshelled Poly(d,1-lactide-co-glycolide) Nanoparticles Carrying Anti p53 Antibody as a Theranostic Agent for Ultrasound Contrast Imaging and Photothermal Therapy, Journal of Biomaterials Science, Polymer Edition, vol. 28, No. 4, pp. 415-430.

Yeh et al., Near-Infrared Light-Responsive Nanomaterials in Cancer Therapeutics, Chem Soc Rev, vol. 43, No. 17, (Sep. 7, 2014), pp. 6177-6474.

Zhao et al., State of the Art in Gold Nanoparticle Synthesis, Coordination Chemistry Reviews, vol. 257, (2013), pp. 638-665.

Baffou et al., Super-Heating and Micro-Bubble Generation around Plasmonic Nanoparticles under cw Illumination, The Journal of Physical Chemistry, vol. 118, (2014), pp. 4890-4898.

Kumar et al., Characterisation of Gold Nanoparticles Synthesised by Leaf and Seed Extract of Syzygium cumini L, Journal of Experimental Nanoscience, vol. 7, No. 4, (Jul.-Aug. 2012), pp. 440-451.

* cited by examiner

VISIBLE UV SPECTRUM

GOLD NANOPARTICLES AND ECOLOGICAL METHOD OF PRODUCTION

CROSS-REFERENCE TO RELATED APPLICATIONS

This application is a national phase entry under 35 U.S.C. § 371 of International Patent Application PCT/FR2017/050131, filed Jan. 23, 2017, designating the United States of America and published as International Patent Publication WO 2017/125695 A1 on Jul. 27, 2017, which claims the benefit under Article 8 of the Patent Cooperation Treaty to French Patent Application Serial No. 1650520, filed Jan. 22, 2016.

TECHNICAL FIELD

This application relates to gold nanoparticles and the medical and cosmetic use thereof. The present disclosure furthermore relates to an ecological method of preparing the nanoparticles from plant extracts and an aqueous solution of gold salts.

The nanoparticles that can be obtained using the method according to the disclosure can be used in several applications, particularly in the medical or cosmetic field, for example, as a catalyzer, sensor, marker for electronic microscopy, gene therapy, an active principle vector, diagnosis, radiotherapy, hyperthermia therapy and imaging.

BACKGROUND

Nanoparticles are being increasingly used in medicine and cosmetics. They may or may not be metallic in nature and their size does not exceed a few hundreds of nanometers. The nature of the nanoparticles provides the latter specific properties.

Gold nanoparticles are highly interesting in nanomedicine. These offer the advantage of having a unique surface plasmon resonance, which makes them particularly interesting in medicine (diagnosis, therapy and research, etc.). Furthermore, they do not oxidize and are inert and biocompatible. Gold nanoparticles can also be coupled with biological molecules such as antibodies, peptides or others, or even inorganic molecules.

Conventionally, metallic nanoparticles were synthesized by chemical processes, the reagents or reaction products of which could be toxic. The reducing agent generally used was citrate (Turkevich, 1951). These processes required washings of the nanoparticles in order to attempt to eliminate toxic agents. These nanoparticles, owing to their method of synthesis, could cause stability, reactivity and biocompatibility problems or even render them unfit for conjugation with biomolecules, with the synthesis reagents resulting in inactivation of the biomolecule.

It has been necessary to develop new methods of synthesis that are more environment-friendly and improve the biocompatibility, stability and reactivity of the gold nanoparticles.

Environment-friendly methods are thus known from the state of the art that use plant extracts to reduce the gold salts. Patent application WO 2005/095031 describes a method for synthesizing mono- and bimetallic nanoparticles of different shapes and sizes via reaction of metallic salts with reducing extracts of different plant parts at a temperature between 15° C. and 100° C. The plants in this patent application are, for example, varieties of cinnamon, lemon, jasmine, chamomile and rose, etc.

U.S. Pat. No. 8,333,994 describes biocompatible gold nanoparticles stabilized with polyphenol-rich or flavonoid-rich plant extracts or phytochemical reactive compounds. The method is environment-friendly. In this patent, an aqueous solution containing gold salts is mixed with polyphenol-rich or flavonoid-rich plant extracts. The solution of gold salts is mixed, for example, with black tea, turmeric or cinnamon.

Methods requiring chemical products have the disadvantage of not being environment-friendly and the gold nanoparticles obtained may pose problems of stability, reactivity, toxicity or biocompatibility, particularly during their subsequent injections into the body owing to dissociation of the (toxic) molecules stabilizing them in solution. These molecules may subsequently be responsible for the side effects observed.

The methods of the state of the art using plant extracts mainly lead to generation of spherical gold particles that are unstable in aqueous solution. It is known that the shape of the nanoparticles directly affects the ability of the nanoparticles to reach the microenvironment of the tumors and, therefore, efficacy of the treatment (Stylianopoulos et al.). The size and shape of the nanoparticles are influenced by the antioxidant composition of the plant extracts. Three factors determine the size and shape of the nanoparticles: the reducing power of the polyphenols, their concentration in the extract and the nature or concentration of the stabilizing agents (Elia et al., 2014). Very often, ecological extraction methods lead to an accumulation of polyphenolic agents of different types (phenolic acids, catechin, epicatechin, anthocyanin flavonoids, tannins, etc.), which do not allow long-term stabilization of the nanoparticles in solution (Krishnaswamy et al., 2014).

In order to increase the efficacy of these nanoparticles, both from the point of view of their ability to reach the target cells and of improving their efficacy, it is essential to find environment-friendly methods that make it possible to obtain monodispersed, stable gold nanoparticles more efficient in generating hyperthermia, which are biocompatible and of a shape that is controlled and uniform.

BRIEF SUMMARY

This disclosure solves the drawbacks of the prior art by an ecological method of preparing biocompatible and stable gold nanoparticles, consisting of reducing metallic salts using at least one flavonoid-rich plant extract, particularly an extract of *Hubertia ambavilla* or *Hypericum lanceolatum*. The gold nanoparticles thus obtained have improved properties in comparison to that of the nanoparticles of the prior art.

A first object of the disclosure concerns an ecological method of preparing biocompatible and stable gold nanoparticles comprising:
  a. Preparation of at least one flavonoid-rich plant extract;
  b. Mixture of at least one of the plant extracts with an aqueous solution of at least one gold salt; and
  wherein the flavonoid-rich plant extract is an extract of *Hubertia ambavilla* or *Hypericum lanceolatum*.

*Hubertia ambavilla* is a species endemic to Reunion Island and Mauritius. This small bush is particularly abundant on Reunion Island, where it is mainly found at between 1000 and 2000 m of altitude. This plant is used in traditional Reunion Island medicine as an herbal tea to treat gastroenteritis in infants or as a decoction to treat skin problems (prickly heat, eczema, burns, itching, wounds and inflammation, etc.). This plant is also reputed to have properties against stomach ulcers and antiviral properties against herpes and the poliomyelitis virus.

*Hypericum lanceolatum* is an arborescent species of St. John's wort native to Reunion Island. It is also known by the name of yellow flower. It is also found in Africa, from Equatorial Guinea to Tanzania. The essential oil of flowers of this plant is used in herbal medicine. This plant is used in Reunion Island traditional medicine in the form of an herbal tea to relieve stomach burns, against urinary infections, to relieve and regulate painful menstrual periods or also against fever. Its antiradical and antioxidant properties are proven.

According to alternative embodiments of the disclosure, a flavonoid-rich plant extract may be a total crude extract of the plant or at least some flavonoids of the plant, particularly:

a total crude extract of *Hubertia ambavilla*;
a total crude extract of *Hypericum lanceolatum*;
the flavonoids of *Hubertia ambavilla*; or
the flavonoids of *Hypericum lanceolatum*.

Advantageously, the plant extract comprises flavonoids selected from among rutin, quercetin, hyperoside and isoquercetin or a combination of at least two thereof.

According to a particular embodiment, the plant extract comprises rutin and quercetin. Advantageously, the plant extract comprising rutin and quercetin is the flavonoids. The flavonoids comprising rutin and quercetin are the flavonoids extracted from *Hypericum lanceolatum*.

According to another embodiment, the plant extract comprises hyperoside and isoquercetin. Advantageously, the plant extract comprising hyperoside and isoquercetin is the flavonoids. The flavonoids comprising hyperoside and isoquercetin are the flavonoids extracted from *Hubertia ambavilla*.

Advantageously, the molar ratio of flavonoids to gold salts is 21 when the method of preparing the gold nanoparticles according to the disclosure involves mixing the solution of gold salts with the flavonoids extracted from *Hubertia ambavilla* or *Hypericum lanceolatum*.

In a preferred embodiment, the flavonoid-rich plant extract employed in the method of preparing gold nanoparticles is a crude extract of *Hubertia ambavilla* or *Hypericum lanceolatum*.

The method according to the disclosure is rapid. The plant extracts and the flavonoids also serve as stabilizers of the nanoparticles once the latter are formed. It, therefore, comprises a limited number of stages. Once the plant extract has been obtained, the method is completed in one stage and in less than a minute. This is much quicker than the chemical methods of the prior art (Frens et al., 1973, Zhao, 2013). By way of example, the chemical composition of the crude extracts of *Hubertia ambavilla* remains highly stable despite the variabilities, of a seasonal nature, observed in the other floral species (Hyperoside/isoquercetin=30). The majority compounds are molecular couples, with a stable ratio, which thus participate in stabilization of the nanoparticles without addition of stabilizing agent.

The nanoparticles that can be obtained using the method according to the disclosure have a diameter of between 5 nm and 100 nm, advantageously between 10 nm and 50 nm.

Two types of nanoparticles are obtained depending on the nature of the plant extract employed in the preparation method.

The nanoparticles obtained by mixing the plant flavonoids with an aqueous solution of at least one gold salt are spherical. Advantageously, these spherical nanoparticles have a diameter of 15 nm.

The nanoparticles obtained by mixing a total crude plant extract with an aqueous solution of at least one gold salt are anisotropic and flower-shaped. Advantageously, these flower-shaped nanoparticles have a diameter of 40 nm to 80 nm.

The two types of nanoparticles obtained according to the method of the disclosure have improved properties versus the nanoparticles described in the state of the art.

A second object of the disclosure concerns anisotropic flower-shaped gold nanoparticles comprising a mixture of gold and crude extract of *Hubertia ambavilla* or *Hypericum lanceolatum*.

This particular "flower" shape is caused by polymerization of the polyphenols in solution, which are simultaneously responsible for reduction of the gold salts, nucleation and growth of the nanoparticles in space along the three axes x, y, z (in other words, three-dimensionally) and their stabilization. The quantity of heat produced by these flower-shaped nanoparticles, when subjected to infrared radiation, is greater than that of the spherical nanoparticles described in the prior art and also to that of the spherical nanoparticles produced by applying the method that is the object of the disclosure. This property definitely results from the electromagnetic interactions of the incident beam with the different surface plasmons of the flower-shaped nanoparticle, allowing an increase in the heat released. Hence, the efficacy of these flower-shaped nanoparticles is increased for the same dose of irradiation. Their increased reactivity versus the nanoparticles of the prior art suggests better therapeutic efficacy. These nanoparticles are furthermore stable and monodispersed. Also, initial results of studies of their biodistribution show that they are capable of accumulating in different organs, particularly in the liver, lung and kidney.

The flower-shaped nanoparticles of the disclosure, obtained by a green chemistry method, have the advantage of not containing any traces of toxic particles, unlike the nanoparticles described in the prior art obtained via a chemical process.

As previously mentioned, these flower-shaped nanoparticles are obtained using the method according to the disclosure when the plant extract is a crude extract of *Hubertia ambavilla* or *Hypericum lanceolatum*.

A third object of the disclosure concerns use of the nanoparticles that can be obtained according to the method disclosed herein in cosmetic, diagnostic and therapeutic applications.

As outlined in the experimental section, the nanoparticles obtained by the method of the disclosure are particularly reactive, mediators of hyperthermia and offer an interesting biodistribution for diagnostic and therapeutic applications.

In cosmetics, they may be included in the formulation of cosmetic products for the skin, hair and nails.

Furthermore, the nanoparticles that can be obtained using the method, which is the object of the disclosure, are soluble in water and are nanotheranostics, i.e., they can be used as diagnostic agents and/or therapeutic agents.

The nanoparticles that can be obtained using the method of the disclosure are present in certain tissues that may develop cancers. They may thus be used both in medical or veterinary imaging techniques and in medical or veterinary treatment methods, for example, hyperthermia by phototherapy.

Advantageously, the cells to be targeted in these imaging or diagnostic methods will be the cells of the liver, lungs and kidneys.

Owing to their properties, the nanoparticles that can be obtained using the method that is the object of the disclosure are particularly suitable for treating cancer.

Generally speaking, gold nanoparticles are biocompatible and have optical properties that allow their use in the medical field (F. Jabeen et al., 2014; Y. Jiang et al., 2015; V. Shanmugam et al., 2014). The possibility of using nanoparticles during in vivo imaging using ultrasound has already been demonstrated (D. R. Arifin et al., 2011). Nanoparticles are also used as part of hyperthermia cancer therapy via infrared radiation; the value of this approach lies in its minimally invasive aspect and in its ease of implementation (J. Song et al., 2016).

Tests have been conducted to obtain nanotheranostic nanoparticles using photothermy and imaging, particularly by combining gold nanoshells with polymers or also with lactic acid (H. Ke et al., 2014). Currently, gold nanoparticles of all shapes and sizes are frequently used in hyperthermia therapy owing to their photosensitivity related to plasmon resonance (Huang, X et al., 2011). Advantage has been taken of this property in treatment of cancer. Application of a laser to the nanoparticles situated at the tumor site causes a local increase in heat. This causes denaturation of the proteins and cell membranes in the immediate surroundings of the nanoparticles, resulting in death of the cancer cells (E. S. Shibu et al., 2013).

The advances in use of gold nanoparticles in hyperthermia treatment of cancer tissues are related to the metal's abilities to absorb and subsequently emit in response infrared rays. In order to implement a therapeutic approach of this kind, it is necessary to study the environment of the tumor to be treated in order to define the appropriate radiation as well as the necessary and permissible temperatures. Work has recently been performed in mathematics in order to model the photothermal effects of nanoparticles in cells and tissues (M. Nabil et al., 2015; S. Peeters et al., 2012). The differences observed in the temperature ranges as a function of the nanoparticles in question led to a modification of the Arrhenius equation (D. Li et al., 2014; C. D. Clark et al., 2011). This allows better selection of nanoparticle sizes and radiation wavelengths to induce appropriate hyperthermia.

The nanoparticles according to the disclosure appear particularly suitable for treating cancer. Indeed, these gold nanoparticles are derived from a so-called "green chemistry" method of synthesis that does not include any toxic compounds. Furthermore, the gold nanoparticles obtained according to the method, which is the object of the disclosure, do not have any traces of toxic product within them. Hence, unlike other nanoparticles, injection of these nanoparticles is not accompanied by any injection of toxic substances, even in trace amounts, into the body. They are, therefore, very safe.

Unlike the current nanotheranostic agents that are not specifically aimed at the cancer targets, the gold nanoparticles obtained according to the method, which is the object of the disclosure, are preferentially found in the lungs, the liver and kidneys, which are tissues in which cancers are frequent, particularly in the liver. Furthermore, they can be functionalized using antibodies specific to antigenic targets of the cancer tissues of interest, as has already been proposed (L. Xu et al., 2017). They may also be functionalized by molecules that are not specific to the target tissues but that encourage addressing of the nanoparticles on the target tissues; these non-specific molecules may, in particular, be molecules included in the specific metabolism of the cells of the target tissue.

Finally, the gold nanoparticles obtained according to the method, which is the object of the disclosure, display a high hyperthermic potential that is advantageous owing to the fact that the dose of irradiation to be delivered will be proportionally less.

Owing to all these properties, the gold nanoparticles obtained according to the method, which is the object of the disclosure, are serious candidates for antitumor applications.

Thus, in one particular embodiment, the disclosure concerns use of the nanoparticles that can be obtained using the method, which is the object of the disclosure, in order to treat cancer. Advantageously, the cancers treated with these nanoparticles will be cancer of the liver, lung and kidney.

In another embodiment, the nanoparticles, which are the object of the disclosure, can be functionalized by any type of molecule allowing targeting thereof in an organ, a tissue or a specific cell type, particularly by means of proteins, particularly antibodies, polymers or sugars.

The present disclosure also concerns a diagnostic and/or treatment method comprising the stages of:
- Administering nanoparticles that can be obtained using the method that is the object of the disclosure;
- Irradiation of the target cells or tissue with an appropriate dose of electromagnetic radiation, for example, infrared rays;
- Detection and/or destruction of the irradiated cells or tissue that have incorporated the nanoparticles.

Advantageously, the target cells or tissue are cancer cells or cancer tissue.

Advantageously, the nanoparticles used in these methods are anisotropic and flower-shaped.

The nanoparticles obtained using the method disclosed herein are monodispersed. They can be administered to humans or animals, for instance, orally or via the intravenous route. They can be tagged or functionalized to improve addressing of the target cells or tissues. They can be coupled with techniques involving electromagnetic waves such as CT scan, MM and SERS RAMAN to detect and/or treat and/or monitor the evolution of various diseases including different types of cancer.

The present disclosure will be better understood in the light of the following examples.

BRIEF DESCRIPTION OF THE DRAWINGS

FIG. 8: Panel A, liver untreated with nanoparticles; Panel B, liver treated with nanoparticles (17 mg; 24 hours).

FIG. 9: Panel A, liver untreated with nanoparticles (27 mg; 24 hours); Panel B, liver treated with nanoparticles (37 mg; 24 hours).

FIG. 10: Panel A, lung untreated with nanoparticles; Panel B, lung treated with nanoparticles (7 mg; 24 hours).

FIG. 11: Panel A, kidney untreated with nanoparticles (7 mg; 24 hours); Panel B, kidney treated with nanoparticles (27 mg; 24 hours).

FIG. 12: kidney treated with nanoparticles (37 mg; 24 hours).

DETAILED DESCRIPTION

Examples

Example 1: Preparation of the Plant Extracts of *Hubertia ambavilla* and *Hypericum lanceolatum*

Two plant species are used in the present disclosure. The first is *Hubertia ambavilla*, which is a bush endemic to Reunion Island. The second is *Hypericum lanceolatum*, which is an arborescent species of St. John's wort native to Reunion Island. Both of these plants are particularly rich in flavonoids, including rutin and quercetin in the case of *Hypericum lanceolatum* and isoquercetin and hyperoside in the case of *Hubertia ambavilla*.

a) Preparation of a Total Crude Plant Extract

Freshly harvested plants are washed in deionized water. Three grams are mixed with 50 mL of deionized water and the mixture is subsequently heated at 60° C. for 5 minutes, which releases the biological material by lysis of plant cells. The supernatant is subsequently cooled to ambient temperature, then on ice for 10 minutes. The cooled supernatant is subsequently filtered over a grade 2 pore size filter.

When the starting material is *Hubertia ambavilla*, the extract obtained is green.

When the starting material is *Hypericum lanceolatum*, the extract obtained is brown.

No organic solvent is used in this preparation.

b) Isolation of the Plant Flavonoids

The extraction method used is a cold maceration method. The plants are crushed on a screen with a pore diameter of 10 mm then left to macerate under stirring at 150 rpm for 20 hours at ambient temperature. A mixture of equal parts of water and ethanol is added to the mixture in a solid/solvent ratio of 1:20 in order to obtain the best possible yield of phenolic compounds (N. Cujic et al.). After extraction, the macerates are filtered, dried under low pressure (maximum bath temperature: 45° C., pressure between 50 and 150 bars) and are subsequently freeze-dried for 48 hours.

The extraction yield for *Hubertia ambavilla* under these conditions is nearly 50%.

Example 2: Preparation of Gold Nanoparticles by Mixing with *Hubertia ambavilla* and *Hypericum lanceolatum* Plant Extracts a) Preparation of the Gold Nanoparticles in Flower Form with the Total Crude Extracts 50 mL of an aqueous solution of 1 mM chloroauric acid ($HAuCl_4$) is refluxed under vigorous stirring in a two-neck round-bottom flask topped by a reflux condenser, protected from light. When fine droplets appear on the walls, 20 mL of an aqueous solution of total crude plant extracts is very quickly added. The solution then rapidly turns midnight blue within 1 minute. The round-bottom flask is subsequently removed from the oil bath and the solution is maintained under vigorous stirring for an additional 15 minutes. The solution is finally maintained at 4° C. protected from light.

The diameter of the nanoparticles thus obtained is measured as described in paragraph c) below.

The nanoparticles obtained have a diameter measured by TEM of approximately 40 nm.

b) Preparation of the Spherical Gold Nanoparticles with the Flavonoids 4 mL of an aqueous solution of the flavonoids is refluxed under vigorous stirring in a two-neck round-bottom flask topped by a reflux condenser, protected from light. When fine droplets appear on the walls, 4 mL of an aqueous solution of $HAuCl_4$ is very quickly added. The solution then rapidly turns red-brown within 1 minute. The round-bottom flask is subsequently removed from the oil bath and the solution is maintained under vigorous stirring for an additional 15 minutes. The solution is finally maintained at 4° C. protected from light.

The diameter of the nanoparticles thus obtained is measured as described in paragraph c) below.

The nanoparticles obtained have a diameter measured by TEM of approximately 15 nm.

A specific molar ratio between the reagents makes it possible to obtain spherical gold nanoparticles. This ratio is as follows:

$n(\text{flavonoids})/n(\text{HAuCl}_4)=21$ c) Characterization of the Nanoparticles Obtained Depending on the Method of Preparation Diameter of the Nanoparticles The diameter of the nanoparticles obtained according to the methods described in paragraphs a) and b) above is measured by transmission electron microscopy (TEM), by dynamic light scattering (DLS) and by atomic force microscopy (AFM).

For the TEM analysis, the electronic microscopy images were recorded on a JEOL JEM 1011 microscope operating at an acceleration voltage of 100 kV.—carbon and dried ambient temperature. For the DLS analysis, the particle size and distribution were recorded on a DLS particle size analyzer (90 Plus Particle Size Analyzer, Brookhaven Instruments Corporation). For the AFM analysis, the samples were characterized by a Molecular Imaging PICOSCAN® II with a MAC extension for "acquisition mode."

The images obtained by TEM show two types of particle: spherical and individual particles 15 nm in diameter obtained with the totum flavonoid extracts and non-spherical, flower-shaped particles obtained with the total crude plant extracts. The latter flower-shaped particles, obtained with the total crude extract of *Hubertia ambavilla* or *Hypericum lanceolatum* have a diameter included between 40 nm-80 nm. It is observed that they are formed of well-individualized particles 15 nm in diameter. The smallest are synthesized with the total of the flavonoids.

The differences observed between the two syntheses suggest that the crude extract is composed of polyphenols, which undergo multidirectional polymerization in space in solution during the chelation stage, resulting in the flower structure.

The data obtained by DLS display two major groups of nanoparticles. The first group consists of individual particles that can polymerize to form the second group, dimers in solution. The results obtained by DLS show an average nanometric particle size greater than that obtained with the TEM and AFM methods. These differences are generally reported in the literature (Elia, 2014). This is due to the DLS method, which measures the hydrodynamic volume by considering the procession of biomolecules (polyphenols) surrounding the particles.

Processing of the image obtained by AFM yields an average size of the flower-shaped nanoparticles of around 33 nm. The individual nanoparticles have an average size of approximately 15 nm.

The sizes of the different nanoparticles measured using the different methods are summarized in Table 1.

AuNP@EBHA=Gold nanoparticles (AuNP) obtained using a crude extract of *Hubertia ambavilla*. AuNP@EBHL=AuNP obtained using a crude extract of *Hypericum lanceolatum*.

AuNP@F2HA=AuNP obtained using a totum of flavonoids of *Hubertia ambavilla*.

TABLE 1

Nanoparticle size according to the measuring method used.

|     | AuNP@EBHA | AuNP@EBHL | AuNP@F2HA |
| --- | --- | --- | --- |
| AFM | Large band: 550-590 nm<br>$\lambda max_{SPR}$ = 550 nm | Large band:<br>500-900 nm<br>$\lambda max_{SPR}$ = 670 nm | Narrow band<br>$\lambda max_{SPR}$ =<br>530 nm |
| TEM | Flower shaped<br>Size: 30-80 nm | Flower shaped<br>Size: 30-80 nm | Spherical<br>Size: 10-15 nm |
| DLS | Average size: 109.7 nm<br>Polydispersity 0.19 | Average size: 82.5 nm<br>Polydispersity 0.28 | ND |

Shapes of the Nanoparticles

Figure 1:
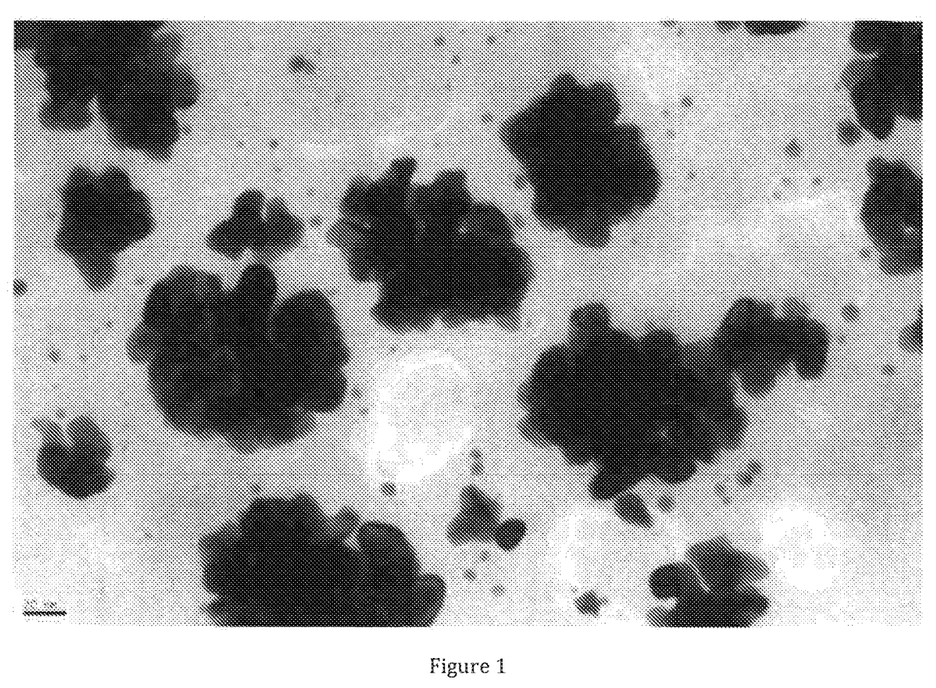
FIG. 1 is a photograph taken by transmission electron microscopy of gold nanoparticles obtained according to the method of the disclosure based on gold salts reduced by a total crude extract of *Hubertia ambavilla* leaves. The nanoparticles obtained have a diameter of 40 nm and are anisotropic and flower-shaped. They are monodispersed.
Figure 2:
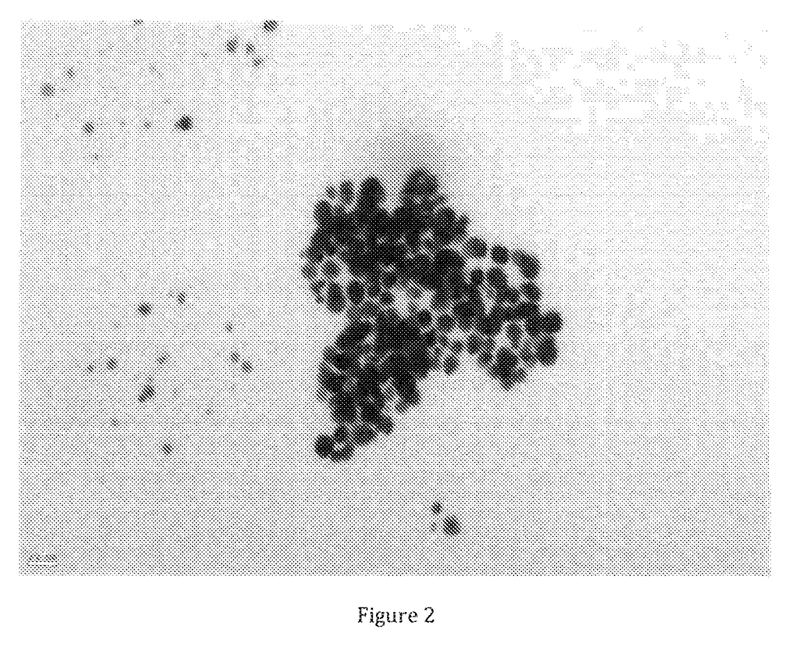
FIG. 2 is a photograph taken by transmission electron microscopy of gold nanoparticles obtained according to the method of the disclosure based on gold salts reduced by the flavonoids of *Hubertia ambavilla* flowers. The nanoparticles obtained have a diameter of 15 nm and are spherical. They are monodispersed.
Figure 3:
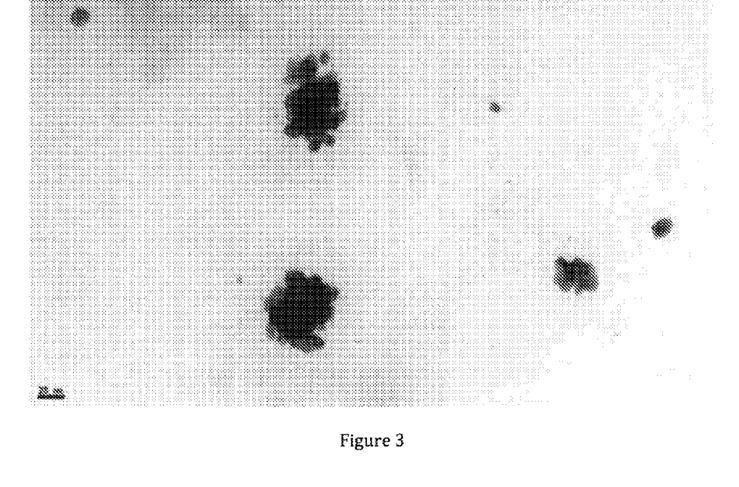
FIG. 3 is a photograph taken by transmission electron microscopy of gold nanoparticles obtained according to the method of the disclosure based on gold salts reduced by a total crude extract of *Hypericum lanceolatum* flowers. The nanoparticles obtained have a diameter of 40 nm and are anisotropic and flower-shaped. They are monodispersed.

FIGS. 1 to 3 show that gold nanoparticles were indeed obtained using the method according to the disclosure. Furthermore, when a total crude plant extract is used, the nanoparticles are anisotropic and flower-shaped, whereas when a totum of flavonoids is used, the gold nanoparticles are spherical and smaller. The nanoparticles obtained using this method are monodispersed.

Figure 4:
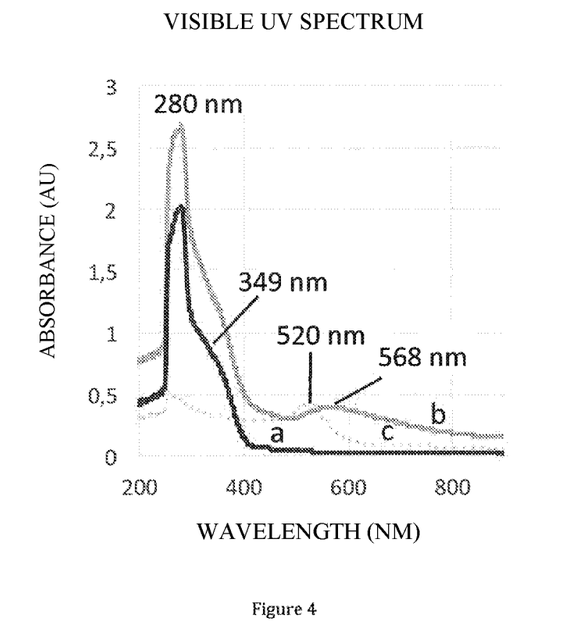
FIG. 4 shows the UV spectrum for the gold nanoparticles obtained using the method according to the disclosure.

The UV spectra of a *Hypericum lanceolatum* extract, of nanoparticles obtained by reaction of the gold salts with a *Hypericum lanceolatum* extract and nanoparticles obtained using the conventional method of Turkevich were compared. FIG. 4 shows the spectra obtained, in a, with the *Hypericum lanceolatum* extracts and, in b, the nanoparticles prepared by reaction with a.

*Hypericum lanceolatum* extract and, in c, the nanoparticles prepared by reaction according to the method of Turkevich are also shown in FIG. 4. In spectrum b, a band appears at 568 nm confirming the presence of flower-shaped, anisotropic gold nanoparticles.

Contrast of the Nanoparticles Studied by Scanner

Feasibility of detection by scanner (CT scan) of the nanoparticles obtained using the method according to the disclosure was verified by tomography. To this end, three samples were scanned by computer-assisted tomography:
Sample no. 1: a drop of gold nanoparticles prepared from citrates according to Turkevich,
Sample no. 2: the supernatant (plant extract alone),
Sample no. 3: a drop of gold nanoparticles prepared from a crude extract of *Hypericum lanceolatum*.

Figure 5:
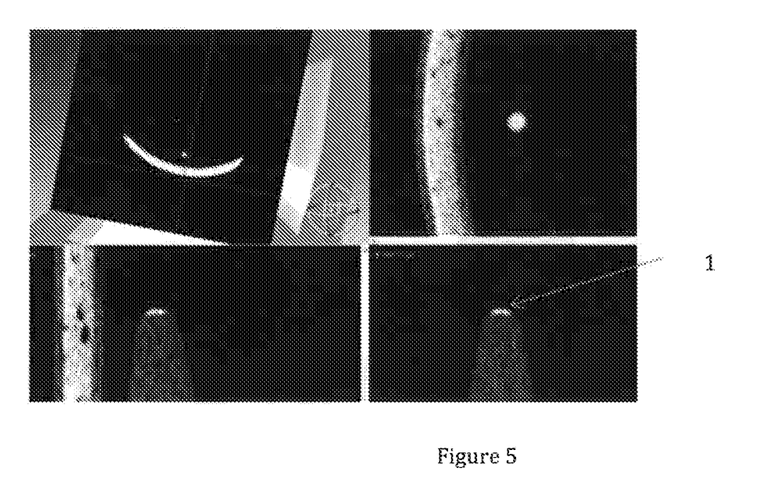
FIG. 5 shows the scan of the gold nanoparticles synthesized using the method according to the disclosure.

The scan shows a drop of nanoparticles synthesized from gold salts and a *Hypericum lanceolatum* extract (sample no. 3). Following ultracentrifugation, samples no. 2 and no. 1 do not exhibit any significant differences in contrast. On the other hand, sample no. 3 shows a black deposit at the bottom of the ultracentrifugation tube displaying a marked contrast (FIG. 5). The radiological contrast of this sample no. 3 at 80 kVp is 621 UH, versus 25 only for the supernatant (sample no. 2) for a concentration of 6 mg Au/Kg, i.e., 15 times less than that of Boote et al. (data not shown).

Boote et al. showed that a linear relationship existed between the gold nanoparticle concentration and the radiological contrast (expressed in HU). In the tests that they performed in vitro, the gold nanoparticles of 20 nm display a radiological contrast of approximately 10 HU at 80 kVp for a concentration of 90 mg Au/Kg. Experiments conducted on mice show a majority accumulation of gold nanoparticles in the liver, with a variation in contrast of between +22.3 HU (per mg Au absorbed/1 $cm^3$) at 80 kVp and +26.7 HU (per mg Au absorbed/1 $cm^3$) at 140 kVp in liver tissues. The data for the spleen show a variation in HU values of between +9.7 HU (mg Au absorbed/1 $cm^3$) at 80 kVp and +10.1 HU (mg Au absorbed/1 $cm^3$) at 140 kVp. Another team (Chanda et al.) showed a radiological contrast of approximately 45 HU at 80 kVp for a concentration of 0.016 M [Au] (i.e., approximately 1.54 g Au/Kg).

Comparison of the results obtained by other teams (given above) with those obtained with the nanoparticles according to the disclosure indicate that the radiological contrast obtained with the nanoparticles obtained using the method that is the object of the disclosure is markedly greater than that previously described. The nanoparticles of the disclosure are, therefore, particularly suitable for imaging.

Yield of Synthesis

The yields of synthesis of the gold nanoparticles obtained using the method of the disclosure employing a total crude plant extract or totum flavonoid extract from the same plant are given in Table 2 below:

TABLE 2

Yield of synthesis of gold nanoparticles with the different plant extracts.

|  | *Hubertia ambavilla* | *Hypericum lanceolatum* |
| --- | --- | --- |
| Total crude extract | 5 g/L | 2.5 g/L |
| Totum of flavonoids | 25 g/L | 30 g/L |

Synthesis with the total crude extract of *Hubertia ambavilla* shows a better yield than synthesis with the total crude extract of *Hypericum lanceolatum*.

The yield of synthesis of gold nanoparticles is slightly greater with the totum of flavonoids of *Hypericum lanceolatum* than with that of *Hubertia ambavilla*.

The yields of synthesis of gold nanoparticles are higher with flavonoid totums than with the total crude extracts.

The yields obtained with the flavonoid totums were compared with the yields obtained with a single flavonoid.

The totum of flavonoids of *Hubertia ambavilla* predominately contains hyperoside and a small amount of isoquercetin. By using the totum of flavonoids of *Hubertia ambavilla* in the method according to the disclosure, spherical, stable gold nanoparticles are obtained. Conversely, reaction of gold salts with isoquercetin alone or with hyperoside alone results in synthesis of unstable gold nanoparticles and a yield of 20 g/L, less than the yield obtained with the flavonoid totum. A synergistic action, therefore, exists between the hyperoside and the isoquercetin.

The totum of flavonoids of *Hypericum lanceolatum* predominately contains rutin and a small amount of quercetin. By using the latter in the method according to the disclosure, spherical, stable gold nanoparticles are obtained. Conversely, the reaction between gold salts and rutin alone or quercetin alone does not allow synthesis of gold nanoparticles. A synergistic action, therefore, exists between the rutin and the quercetin.

Example 3: Study of the Photothermy of the Gold Nanoparticles In Vitro

The ability of the nanoparticles to emit heat under infrared irradiation was studied in vitro. The AuNP used in this experiment were obtained by mixture with a totum of flavonoids of *Hubertia ambavilla*.

It is known that gold nanoparticles offer a high potential for treating tumors by hyperthermia. Their efficacy, however, will depend on their size, shape and surface state.

With the aim of assessing the laser irradiation power of the sample around the plasmon resonance of the nanoparticles used as well as the exposure time required to achieve a sufficient temperature for photothermal treatment of the cells, generation of microbubbles under continuous illumination of the waves was studied. According to Baffou et al. (*J. Phys. Chem. C* 2014, 118:4890), the local temperature required to initiate generation of bubbles is approximately 220° C.

Results

Figure 6:
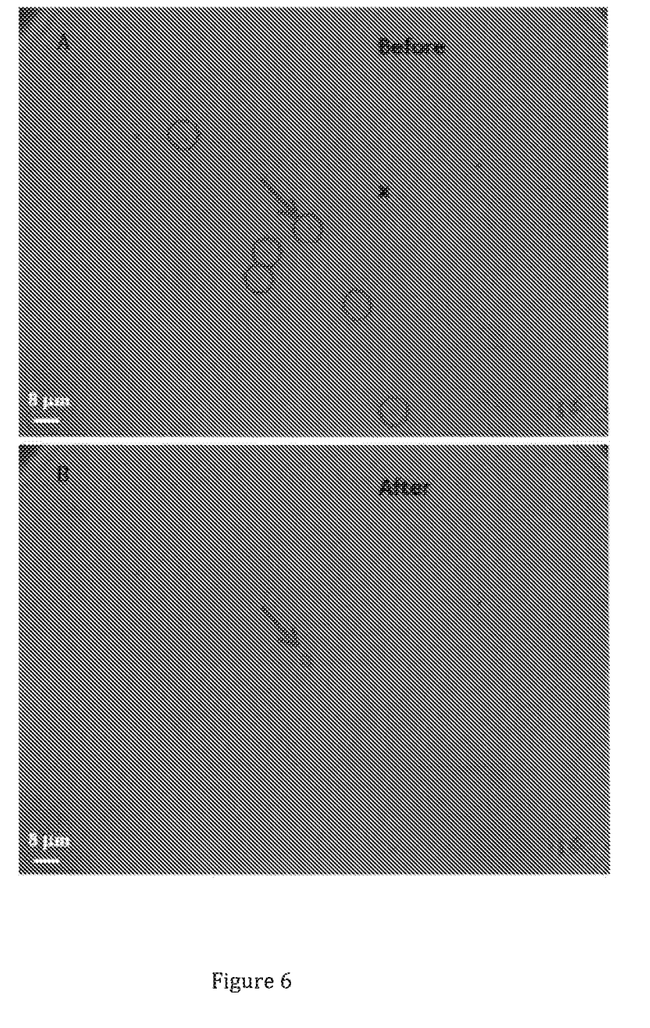
FIG. 6 shows in Panel A an optical image (light field) of a glass slide with a colloidal nanoparticle applied (certain absorbent aggregates are circled). The aggregate indicated by an arrow in Panels A and B was targeted with the laser light (9.5 mW/$\mu m^2$ for 5 seconds). In Panel B, a microbubble is formed at the nanoparticle level. The laser was subsequently focused on the position identified by X (no colloids); no bubble is formed in this case.

Small aggregates of nanoparticles were visualized by optical microscopy using an 80×, 0.75 NA lens. The smallest black spots observed in the bright field are likely to correspond to aggregates about 200 nm in size (FIG. 6, Panel A). It was not possible to locate individual nanoparticles owing to the diffraction limit. After having recorded a first optical image with the laser switched off, the laser light (exc=660 nm) was focused on the aggregate for a fixed period. A second optical image was subsequently recorded after cutting the laser light off. As shown in FIG. 6, Panel B, a microbubble was formed with an exposure of 5 seconds and an irradiation of 9.5 mW/μm². The same experiment was repeated five times on other aggregates of similar size, always resulting in formation of microbubbles for exposure periods of between 2 to 5 seconds with the same laser irradiation. Greater irradiation results in larger bubbles.

Figure 7:
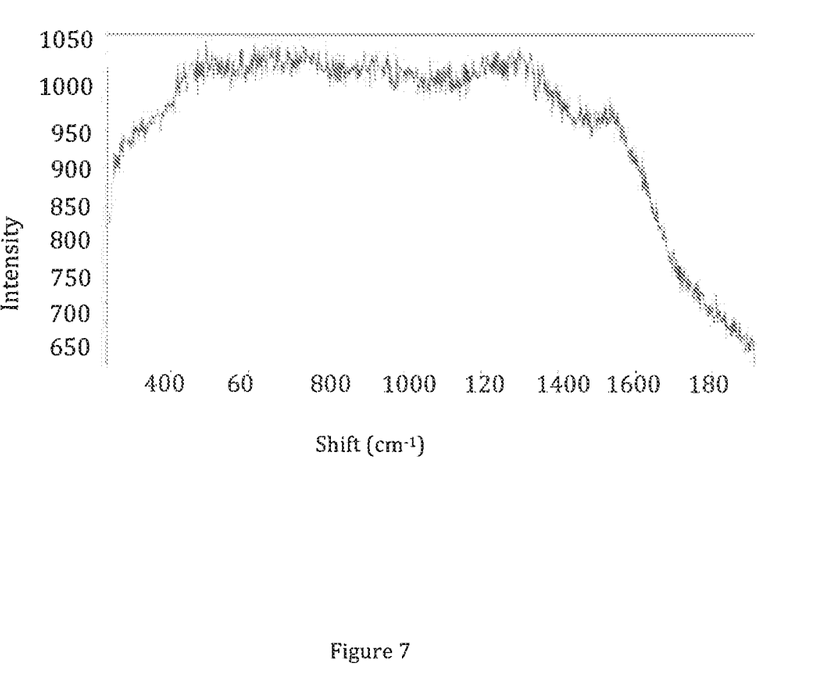
FIG. 7 shows the Raman spectra obtained during focusing on a small aggregate of nanoparticles applied to glass and surrounded by water ($\lambda exc=660$ nm, P=2 mW/$\mu m^2$, integration time of 5 seconds). Represented as ordinate (y) is the intensity in pulses/minute and as abscissa (x) the wave number ($cm^{-1}$).
Figure 8:
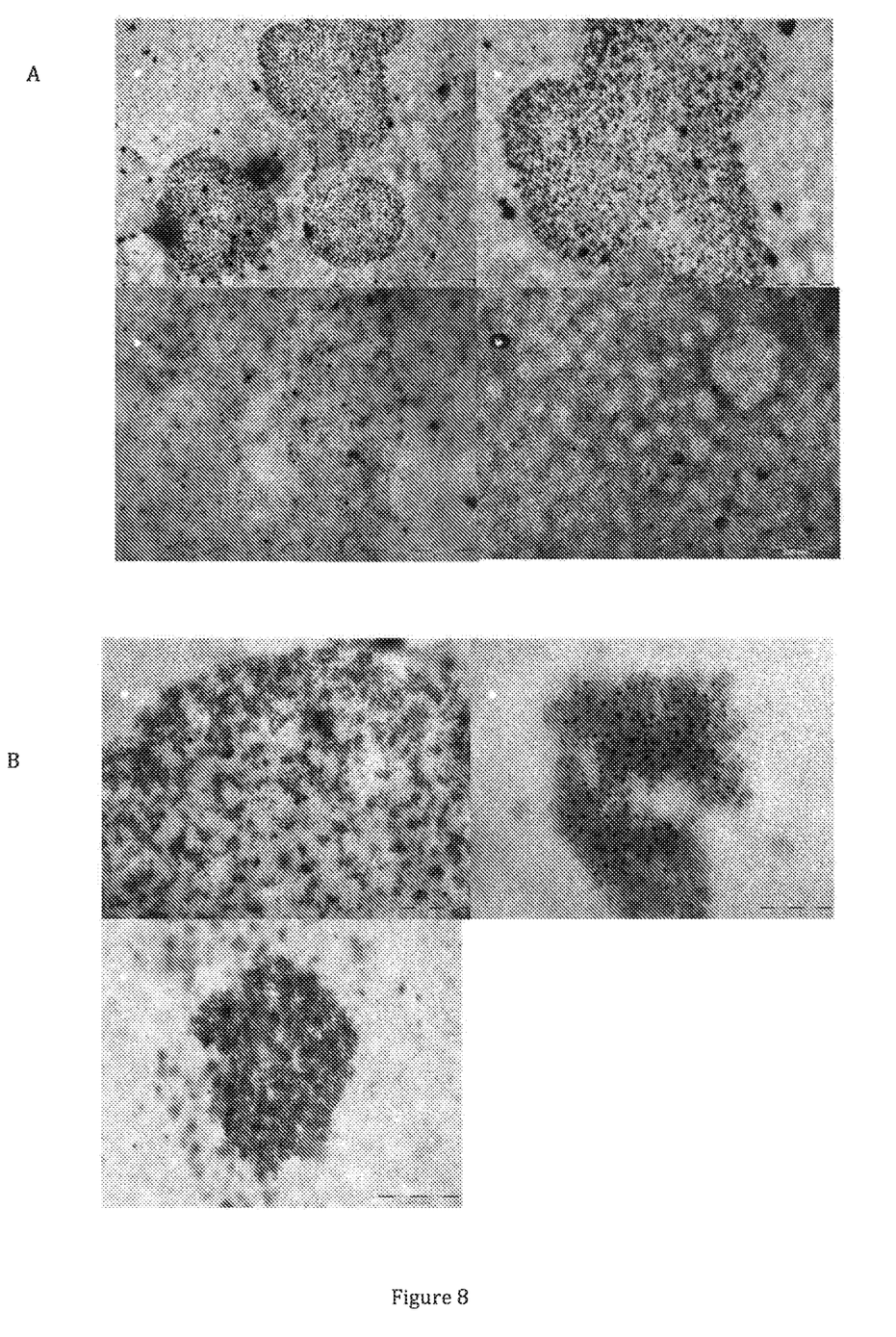
FIGS. 8 to 12 are photographs taken by TEM of sections of tissue from mice having received gold nanoparticles. The nanoparticles appear in the form of black dots.
Figure 9:
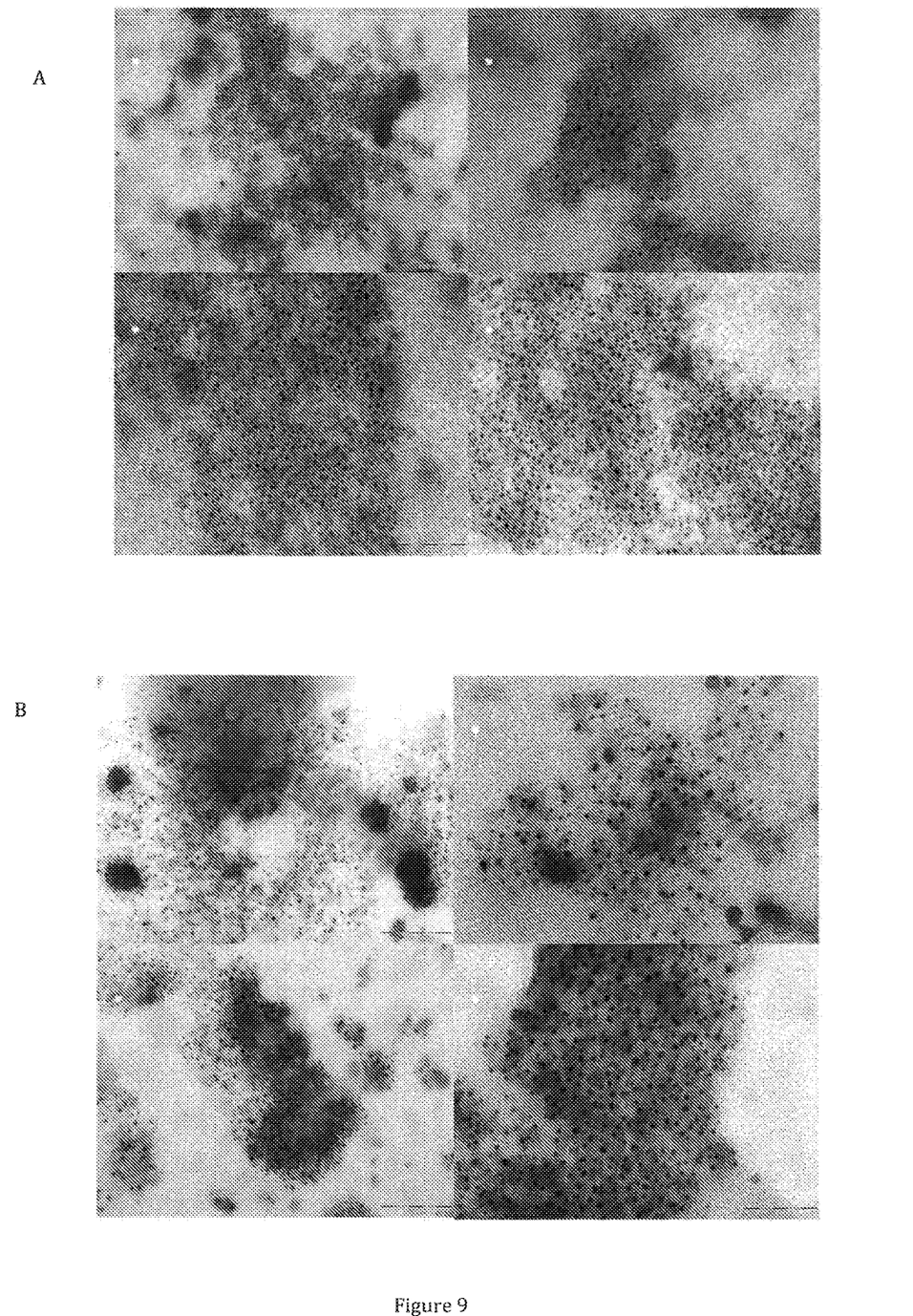
Figure 10:
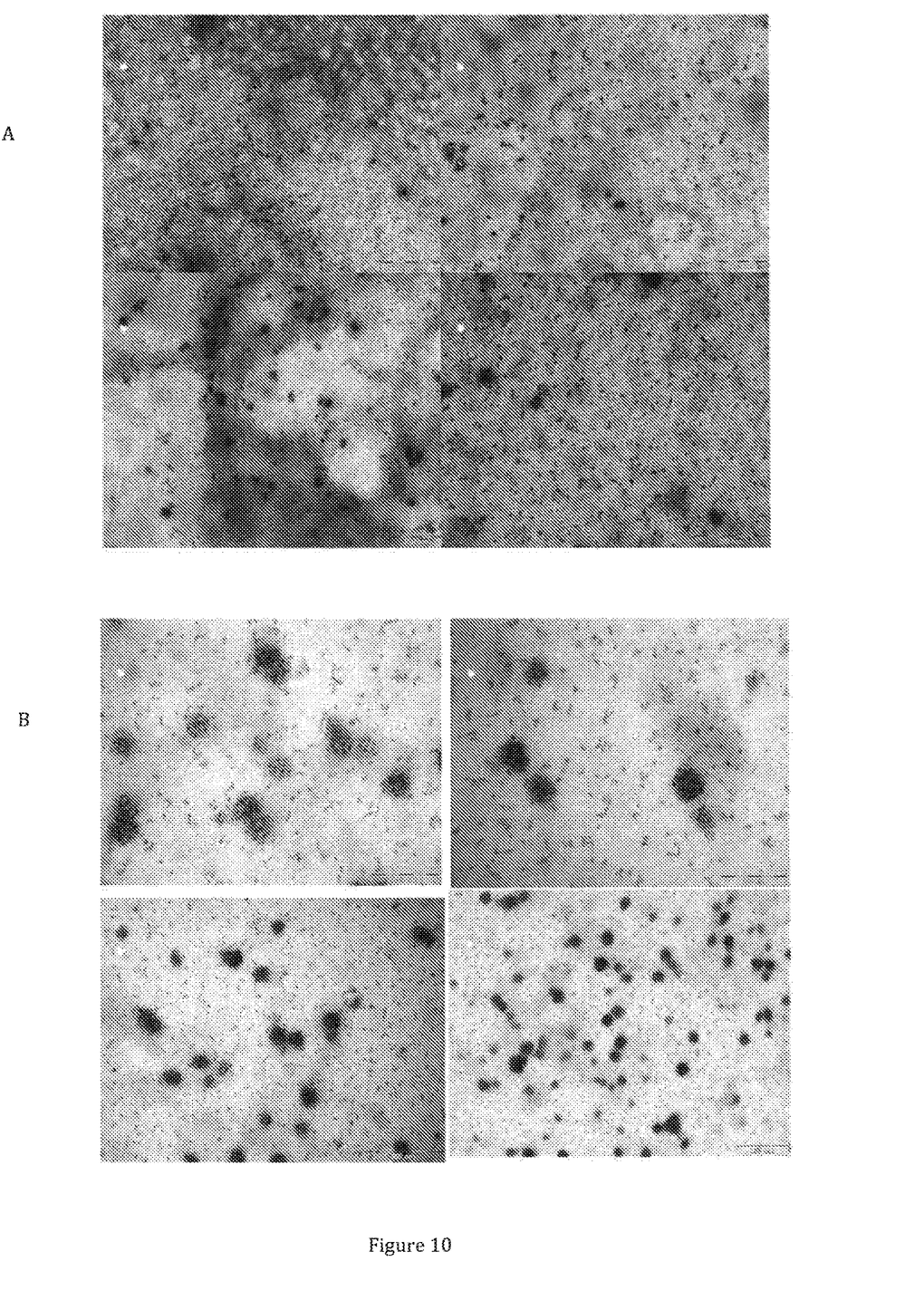
Figure 11:
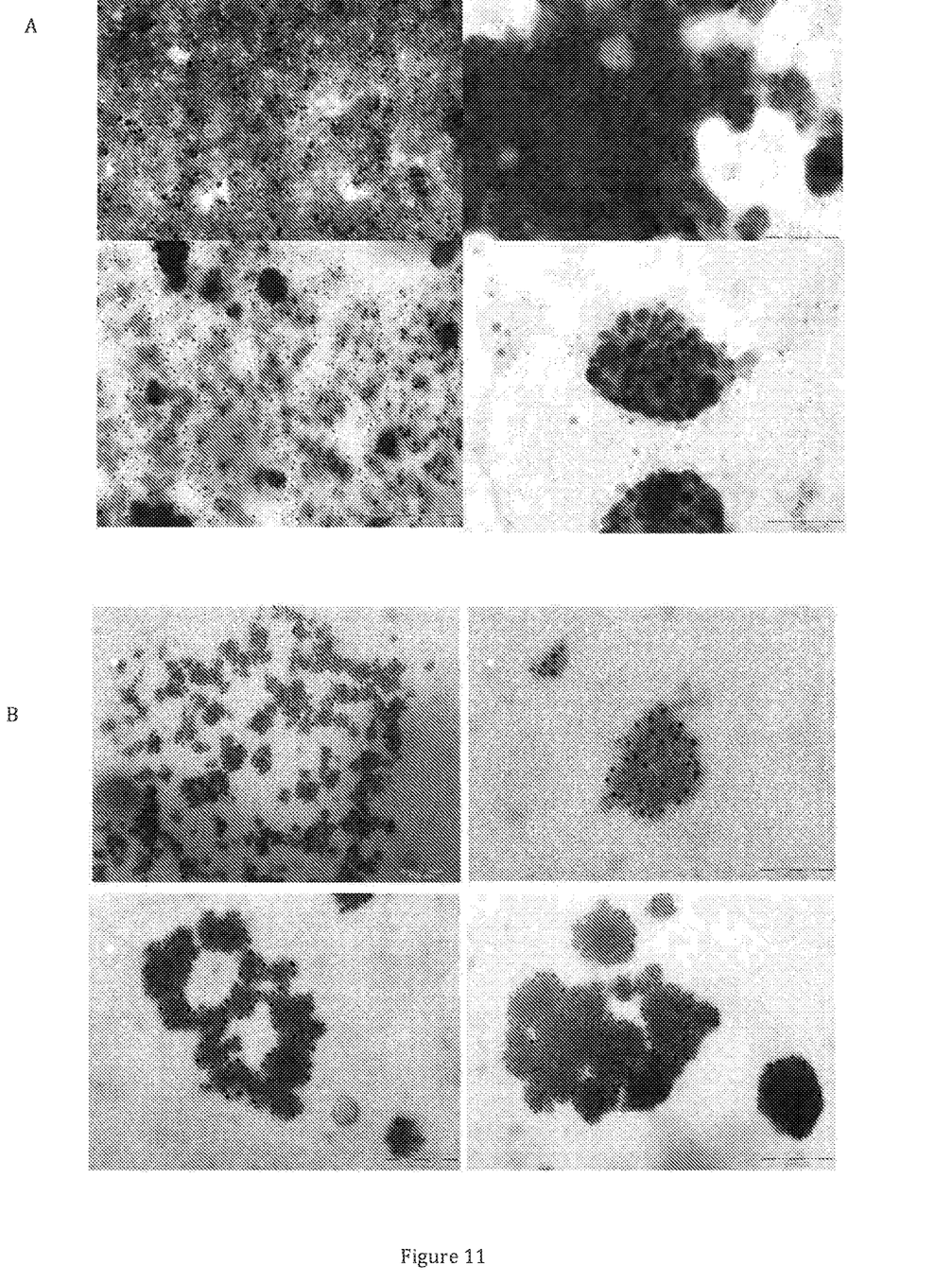
Figure 12:
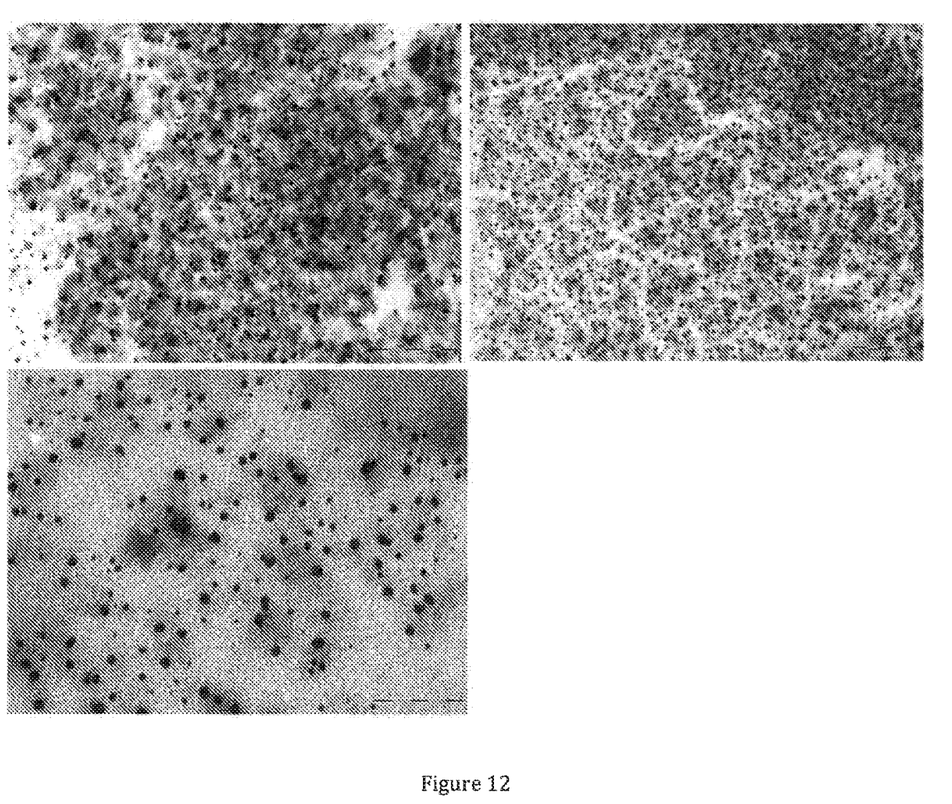

Negative tests were also performed when focusing the laser light away from the aggregate of nanoparticles; no bubble is formed (position X in FIG. 6, Panel A). The bubbles are generated at NP level and are due to plasmon absorption of the NP. Furthermore, irradiation of similar aggregates with 5 mW/μm² for 30 seconds does not produce any microbubbles. The bubble formation threshold (T~220° C.) is included between 5 and 9.5 mW/μm² of laser irradiation. As the threshold occurs at high temperature, it could be assumed that the temperature and, therefore, the power necessary to induce cell death ought to be lower. Laser irradiation >6 mW/μm² was selected for the photothermal measurements previously presented on the immobilized cells. A weak Raman signal (broad bands of amorphous carbon at ~1300 and ~1550 cm$^{-1}$) can be detected from the NP aggregates using 2 mW/μm² for 5 seconds (FIG. 7). The signal is still present after formation of the bubble (i.e., after heating), but with a much lower background.

The plasmon band of the gold nanoparticles of the disclosure is located between 600 nm and 700 nm, offset by more than 100 nm in relation to the individual nanoparticles in solution. This offset may be the result of two phenomena. The first corresponds to the change of environment during nanoparticle internalization. In this case, the nanoparticle may be covered by proteins or other biological molecules, which will cause a redshift of the plasmon resonance. The second phenomenon corresponds to aggregation of the nanoparticles in the cell medium, confirming the observations by dark field microscopy. The plasmon resonances of the nanoparticles are close to the longest irradiation wavelengths (808 nm) considered less energetic and, therefore, less destructive to the living organism.

Example 4: Study of In Vivo Biodistribution of the Gold Nanoparticles

Equipment and Methods

Animal models: The mice used in this experimental protocol are male Swiss mice weighing 20 g to 30 g and 6 weeks of age obtained from R. Janvier.

Synthesis of gold nanoparticles: The nanoparticles were synthesized ecologically according to the methods of the present disclosure and characterized by TEM, DLS and AFM. The gold nanoparticles (AuNP) were injected into the mice intravenously in order to conduct the biodistribution study. All the AuNP were administered following centrifugation; stabilized in an aqueous solution.

Description of the experimental protocol: An injection of 200 μL of the different solutions was performed via the intravenous route. 200 μL was administered for a mouse weighing approximately 24 g.

The following solutions were injected according to the protocols already described by Boote et al., 2010, and Chanda et al., 2014:

NaCl (6 mice)
Product 1 (AuNP@EBHL=AuNP obtained using a crude extract of *Hypericum lanceolatum*)
  Group A (6 mice)=one single injection of 7 mg/ml
  Group B (6 mice)=one single injection of 2 mg/ml
Product 2 (AuNP@EBHA_A=AuNP obtained using a crude extract of *Hubertia ambavilla*)
  Group A (6 mice)=one single injection of 7 mg/ml
  Group B (6 mice)=one single injection of 2 mg/ml
Product 3 (AuNP@F2HA obtained using a totum of flavonoids of *Hubertia ambavilla*)
  Group A (6 mice)=one single injection of 7 mg/ml
  Group B (6 mice)=one single injection of 2 mg/ml That is, a total of 42 mice.

These mice were subsequently separated into three groups for each concentration of each product.

The first group was killed after 6 hours (three mice per product and per concentration, i.e., a total of 27 mice) and the second group was killed after 24 hours.

Finally, samples of the different organs were taken (Liver, Brain, Spleen, Lung and Heart) in order to study biodistribution of the different products.

Results

Following injection of the AuNP via the intravenous route, the organ extracts were analyzed by TEM in order to locate the nanoparticles.

The nanoparticles were found accumulated in the following organs: lungs, kidneys and liver. The results corresponding to the mice injected with product 3 are illustrated in FIGS. 8 to 12. Similar biodistribution is obtained with products 1 and 2 (data not shown).

These results show that the quantity of AuNP found in the different organs is proportional to the quantity administered.

REFERENCES

N. Cujic, K. Savikin, T. Jankovic, D. Pljevljakusic, G. Zdunic, S. Ibric, 2016. Optimization of polyphenols extraction from dried chokeberry using maceration as traditional technique. *Food Chemistry* 194:135-142.

T. Stylianopoulos and R. K. Jain. "Design considerations for nanotherapeutics in oncology." *Nanomedicine: Nanotechnology, Biology and Medicine* 11(8):1893-1907.

J. Turkevich, P. C. Stevenson and J. Hiller. "A study of the nucleation and growth processes in the synthesis of colloidal gold." *Discussions of the Faraday Soc.* 1951, 11:55.

F. Jabeen, M. Najam-ul-Haq, R. Javeed, C. W. Huck, and G. K. Bonn. Au-nanomaterials as a superior choice for near-infrared photothermal therapy. *Molécules* (Basel, Switzerland). 2014; 19:20580-93.

Y. Jiang, W. Fei, X. Cen, Y. Tang, and X. Liang. Near-infrared Light Activatable Multimodal Gold Nanostructures Platform: An Emerging Paradigm for Cancer Therapy. *Current Cancer Drug Targets* 2015, 15:406-22.

V. Shanmugam, S. Selvakumar, and C. S. Yeh. Near-infrared light-responsive nanomaterials in cancer therapeutics. *Chemical Society Reviews* 2014, 43:6254-87.

D. R. Arifin, C. M. Long, A. A. Gilad, C. Alric, S. Roux, O. Tillement, T. W. Link, A. Arepally, and J. W. Bulte. Trimodal gadolinium-gold microcapsules containing pancreatic islet cells restore normoglycemia in diabetic mice and can be tracked by using US, CT, and positive-contrast MR imaging. *Radiology* 2011, 260:790-8.

J. Song, J. Qu, M. T. Swihart, and P. N. Prasad. Near-IR responsive nanostructures for nanobiophotonics: emerging impacts on nanomedicine. *Nanomedicine: Nanotechnology, Biology, and Medicine* 2016, 12:771-88.

H. Ke, X. Yue, J. Wang, S. Xing, Q. Zhang, Z. Dai, J. Tian, S. Wang, and Y. Jin. Gold nanoshelled liquid perfluorocarbon nanocapsules for combined dual modal ultrasound/CT imaging and photothermal therapy of cancer. *Small.* 2014, 10:1220-7.

X. Huang, and M. A. El-Sayed. Plasmonic photo-thermal therapy (PPTT). *Alex. J. Med.* 2011, 47:1-9.

M. A. Mackey, M. R. K. Ali, L. A. Austin, R. D. Near, and M. A. El-Sayed. The most effective gold nanorod size for plasmonic photothermal therapy: Theory and in vitro experiments. *J. Phys. Chem.* B2014, 118:1319-1326.

E. S. Shibu, M. Hamada, N. Murase, and V. Biju. *J Photoch. Photobio.* C 2013, 15:53.

M. Nabil, P. Decuzzi, and P. Zunino. Modelling mass and heat transfer in nano-based cancer hyperthermia. *R. Soc. Open Sci.* 2015, 2:150447.

S. Peeters, M. Kitz, S. Preisser, A. Wetterwald, B. Rothen, B. Rutishauser, G. N. Thalmann, C. Brandenberger, A. Bailey, and M. Frenz. Mechanisms of nanoparticle-mediated photomechanical cell damage. *Biomed. Opt. Express.* 2012, 3:435-446.

D. Li, G. X. Wang, Y. L. He, W. J. Wu, and B. Chen. A three-temperature model of selective photothermolysis for laser treatment of port wine stain containing large malformed blood vessels. *Appl. Therm. Eng.* 2014, 65:308-321.

C. D. Clark, M. L. Denton, and R. J. Thomas. Mathematical model that describes the transition from thermal to photochemical damage in retinal pigment epithelial cell culture. *J. Biomed. Opt.* 2011, 16:020504.

L. Xu, C. Wan, J. Du, H. Li, X. Liu, H. Yang, and F. Li. Synthesis, characterization, and in vitro evaluation of targeted gold nanoshelled poly (D,L-lactide-co-glycolide) nanoparticles carrying anti p53 antibody as a theranostic agent for ultrasound contrast imaging and photothermal therapy. *J. Biomater. Sci. Polym. Ed.* 2017 Jan. 3:1-37.

K. Krishnaswamy, H. Vali, and V. Orsat (2014). Value-adding to grape waste: Green synthesis of gold nanoparticles. *Journal of Food Engineering*, 142:210-220.

P. Elia, R. Zach, S. Hazan, S. Kolusheva, Z. E. Porat, and Y. Zeiri (2014). Green synthesis of gold nanoparticles using plant extracts as reducing agents. *International Journal of Nanomedicine*, 9:4007.

E. Boote, G. Fent, V. Kattumuri, S. Casteel, K. Katti, N. Chanda, and R. Churchill (2010). Gold nanoparticle contrast in a phantom and juvenile swine: models for molecular imaging of human organs using x-ray computed tomography. *Academic Radiology*, 17(4):410-417.

N. Chanda, A. Upendran, E. J. Boote, A. Zambre, S. Axiak, K. Selting, and J. Singh (2014). Gold nanoparticle based X-ray contrast agent for tumor imaging in mice and dog: a potential nanoplatform for computer tomography theranostics. *Journal of Biomedical Nanotechnology*, 10(3): 383-392.

G. Frens (1973). Controlled nucleation for the regulation of the particle size in monodisperse gold suspensions. *Nature*, 241(105):20-22.

J. Turkevich, P. C. Stevenson, and J. Hillier (1951). A study of the nucleation and growth processes in the synthesis of colloidal gold. *Discussions of the Faraday Society*, 11:55-75.

P. Zhao, N. Li, and D. Astruc (2013). State of the art in gold nanoparticle synthesis. *Coordination Chemistry Reviews*, 257(3): 638-665.

The invention claimed is:

1. A method of preparing biocompatible and stable gold nanoparticles, comprising:
    preparing at least one total crude plant extract; and
    mixing at least one of the total crude plant extracts with an aqueous solution of at least one gold salt in a single step,
    wherein the total crude plant extract is an extract of *Hubertia ambavilla* or *Hypericum lanceolatum*.

2. The method of claim 1, wherein the total crude plant extract comprises flavonoids selected from among rutin, quercetin, hyperoside and isoquercetin or a combination of at least two thereof.

3. The method of claim 1, wherein the nanoparticles have a diameter of between 5 and 100 nm.

4. The method of claim 1, wherein the nanoparticles are anisotropic and flower-shaped, and the flower-shaped gold nanoparticles are obtained by mixing a total crude plant extract with an aqueous solution of at least one gold salt.

5. The method of claim 4, wherein a metal of the flower-shaped gold nanoparticles consists of gold.

* * * * *